(12) United States Patent
Yoshioka

(10) Patent No.: US 8,343,440 B2
(45) Date of Patent: Jan. 1, 2013

(54) CELL SEPARATING APPARATUS AND CELL SEPARATING METHOD

(75) Inventor: Satomi Yoshioka, Shiojiri (JP)

(73) Assignee: Seiko Epson Corporation (JP)

( * ) Notice: Subject to any disclaimer, the term of this patent is extended or adjusted under 35 U.S.C. 154(b) by 137 days.

(21) Appl. No.: 12/729,572

(22) Filed: Mar. 23, 2010

(65) Prior Publication Data

US 2010/0248358 A1 Sep. 30, 2010

(30) Foreign Application Priority Data

Mar. 27, 2009 (JP) ................................ 2009-078461
Sep. 14, 2009 (JP) ................................ 2009-211500

(51) Int. Cl.
*B01L 3/00* (2006.01)
(52) U.S. Cl. ............... 422/502; 422/527; 424/155.1; 435/2; 435/3; 435/7.1; 435/7.2; 435/7.21; 435/7.22; 435/7.23; 435/173.4; 435/173.9; 435/325; 435/347; 435/286.1; 435/287.2; 435/287.3; 435/287.9; 435/308.1; 436/524; 436/64; 436/55; 436/63; 436/177; 436/824; 436/813
(58) Field of Classification Search ............... 422/527; 424/155.1; 435/2, 3, 7.1–7.23, 173.1, 173.4, 435/173.9, 325, 347, 286.1, 287.2, 287.3, 435/287.9, 308.1; 436/425, 64, 55, 63, 177, 436/824, 813
See application file for complete search history.

(56) References Cited

U.S. PATENT DOCUMENTS 5,147,607 A * 9/1992 Mochida ................ 422/417
7,842,514 B2 11/2010 Hattori et al.

2003/0129671 A1* 7/2003 Wilding et al. ............ 435/7.2
2006/0252087 A1* 11/2006 Tang et al. ................. 435/6
2007/0207548 A1* 9/2007 Blankenstein ............. 436/63

FOREIGN PATENT DOCUMENTS

| JP | 2002-503334 | 1/2002 |
| JP | 2004-354364 | 12/2004 |
| JP | 2008-310786 | 12/2008 |
| WO | 98-10267 | 3/1998 |

OTHER PUBLICATIONS

Nagrath, Sunitha et al., "Isolation of Rare Circulating Tumour Cells in Cancer Patients by Microchip Technology", Nature Publishing Group, vol. 450, pp. 1235-1239 and p. 6385, Dec. 20, 2007.
Sequist, Lecia V., M.D. et al., "The CTC-Chip, An Exciting New Tool to Detect Circulating Tumor Cells in Lung Cancer Patients", Pathway of the Month, Journal of Thoracic Oncology, vol. 4, No. 3, pp. 281-283, Mar. 2009.
Hessel, Dr. Volker et al., "Liquid- and Liquid/Liquid-Phase Reactions", Sections 4.9-4.11, Chemical Micro Process Engineering: Fundamentals, Modelling and Reactions, pp. 390-391, Jan. 28, 2005.
Continuous Separation of Cells of High Osteoblastic Differentiation Potential From Messenchymal Stem Cells on an Antibody Immobilized Column, by Atsushi Mahara and Tetsuji Yamaoka, Biomaterials, vol. 31, Issue 14, May 2010, pp. 4231-4237.

* cited by examiner

*Primary Examiner* — Melanie J Yu
*Assistant Examiner* — Erik B Crawford
(74) *Attorney, Agent, or Firm* — Harness, Dickey & Pierce, P.L.C.

(57) ABSTRACT

A cancer cell separating apparatus includes: a flow channel including an antibody fixation area having antibodies which bind specifically to cancer cells fixed thereon, wherein the cancer cells and non-cancer cells are separated using a difference in velocity of movement between the cancer cells and the non-cancer cells in cell slurry introduced into the flow channel.

2 Claims, 7 Drawing Sheets

CELL SEPARATING APPARATUS AND CELL SEPARATING METHOD

Japanese Patent Application No. 2009-78461 filed on Mar. 27, 2009, No. 2009-211500 filed on Sep. 14, 2009, are hereby incorporated by reference in its entirety.

BACKGROUND

1. Technical Field

The present invention relates to a cancer cell separating apparatus and a cancer cell separating method which is capable of separating cancer cells from non-cancer cells.

2. Related Art

In all countries in the world, cancer is one of principal causes of death. Most of the reasons of death due to the cancer are re-occurrence of cancer on the basis of metastasis. Cancer cells are fixed to a blood vessel wall of another tissue via a blood vessel or a lymph duct, are infiltrated therethrough and form minute metastasis new focus, so that the metastasis of cancer from a primary focus is established.

Today, chemotherapeutics and radiotherapeutics are widely performed as a method of preventing the metastasis of cancer (JP-A-2008-310786). However, there are cases where sufficient effects cannot be achieved.

JP-A-2008-310786 is an example of related art.

SUMMARY

An advantage of some aspects of the invention is to provide a cancer cell separating apparatus and a cancer cell separating method which is capable of separating cancer cells reliably from cell slurry.

According to an aspect of the invention, there is provided a cancer cell separating apparatus including: a flow channel including an antibody fixation area having antibodies which bind specifically to cancer cells fixed thereon, in which the cancer cells and non-cancer cells are separated using a difference in velocity of movement between the cancer cells and the non-cancer cells in cell slurry introduced into the flow channel.

Preferably, the antibody fixation area is provided on an entire surface of the flow channel.

Preferably, the flow channel includes: a first portion; and a second portion and a third portion bifurcated from an one end portion of the first portion, in which an antibody fixation prohibited area having no antibody fixed thereon is provided on the surface of the first portion on the side of the second portion, and the antibody fixation area is provided on the surface of the first portion on the side of the third portion.

Preferably, a first electrode pair and a second electrode pair are further included, and time lengths required for the cancer cells and the non-cancer cells to pass from the first electrode pair to the second electrode pair are detected. In this case, the cancer cell separating apparatus may further include a dielectric migration electrode pair. In addition, in this case, the cancer cell separating apparatus may control the dielectric migration electrode pair on the basis of the time length.

A cancer cell separating method according to a second aspect of the invention includes introducing cell slurry into a flow channel including an antibody fixation area having antibodies which bind specifically to cancer cells fixed thereon and separating the cancer cells from non-cancer cells using a difference in velocity of movement between the cancer cells and the non-cancer cells in the cell slurry.

According to the cancer cell separating method described above, damages to cells themselves are minimized, and the cancer cells may be removed selectively and with high degree of accuracy by separating the cancer cells from the non-cancer cells using the difference in velocity of movement between the cancer cells and the non-cancer cells in the cell slurry introduced into the flow channel. Since a flow channel having a complicated structure is not necessary for separating the cancer cells, the cancer cells can be separated with the flow channel in a simple structure, so that reduction of cost required for manufacturing the flow channel is achieved. Furthermore, by selecting the types of the antibodies to be fixed to the surface of the flow channel, removal of a wide variety of the cancer cells is accommodated.

According to a third aspect of the invention, there is provided a cancer cell separating apparatus including a primary flow channel for allowing cell slurry to be introduced; and a first secondary flow channel which is branched from a first branch portion provided in the primary flow channel and joins the primary flow channel at a first joint portion provided at a predetermined distance from the first branch portion of the primary flow channel, in which an antibody fixation area having antibodies which bind specifically to cancer cells fixed thereon is provided on an inner wall surface of the primary flow channel on the side of the first secondary flow channel and the inner wall surface of the first secondary flow channel on the side apart from the primary flow channel.

Preferably, second to $n^{th}$ secondary flow channels (here, n represents integer numbers of 2 or larger) are provided, and a $k^{th}$ secondary flow channel (here, k represents integer numbers from 2 to n) is branched from a $k^{th}$ branch portion provided in a $k-1^{th}$ secondary flow channel, and joins the primary flow channel at a $k^{th}$ joint portion provided at a predetermined distance from a $k-1^{th}$ joint portion of the primary flow channel, and the antibody fixation area having the antibodies which bind specifically to the cancer cells fixed thereon is provided on the inner wall surface of the $k^{th}$ secondary flow channel on the side apart from the primary flow channel.

Preferably, a first electrode pair; a second electrode pair provided downstream from the first electrode pair; and a dielectric migration electrode pair provided downstream from the second electrode pair are further provided, and a first time length required for the cancer cells to pass from the first electrode pair to the second electrode pair and a second time length required for non-cancer cells different from the cancer cells passing from the first electrode pair to the second electrode pair are detected, and the dielectric migration electrode pair is controlled on the basis of the first time length and the second time length.

According to the cancer cell separating apparatus described above, since the first secondary flow channel which is branched from the first branch portion provided in the primary flow channel and joins the primary flow channel at the first joint portion provided at a predetermined distance from the first branch portion of the primary flow channel is provided, the non-cancer cells and components separated from the cancer cells are collected.

According to the cancer cell separating apparatus described above, since the antibody fixation areas are provided on the inner wall surface of the primary flow channel on the side of the first secondary flow channel and on the inner wall surface of the first secondary flow channel on the side apart from the primary flow channel, the cancer cells are removed with high degree of accuracy and selectively with a little damages to cells themselves.

Furthermore, according to the cancer cell separating apparatus described above, by selecting the types of the antibodies to be fixed to the inner wall surface of the flow channel, removal of a wide variety of the cancer cells is accommodated.

BRIEF DESCRIPTION OF THE DRAWINGS

The invention will be described with reference to the accompanying drawings, wherein like numbers reference like elements.

DESCRIPTION OF EXEMPLARY EMBODIMENTS

A cancer cell separating apparatus and a cancer cell separating method according to an embodiment of the invention will be described in detail below.

Figure 1:
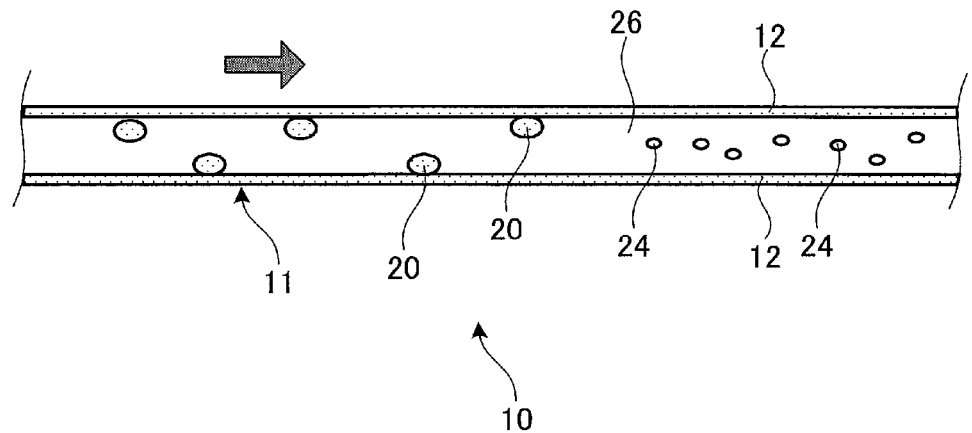
FIG. 1 is a cross-sectional view diagrammatically showing a cancer cell separating apparatus according to a first embodiment of the invention.
Figure 2:
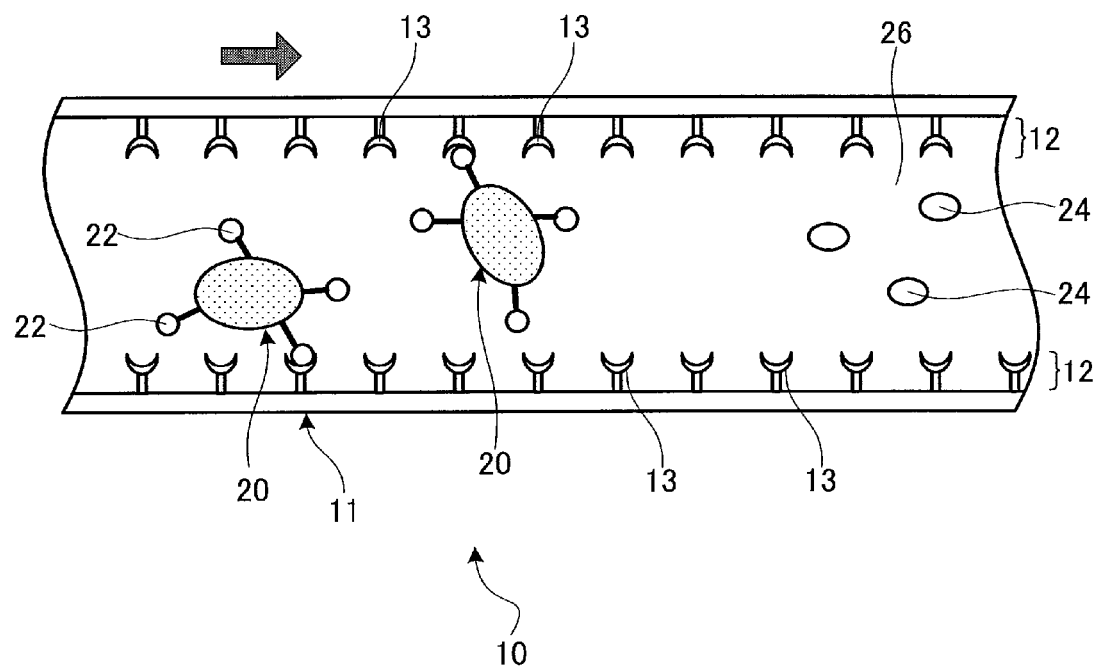
FIG. 2 is an explanatory drawing showing a cancer cell separating method by the cancer cell separating apparatus shown in FIG. 1.

1. First Embodiment 1.1. Configuration of Cancer Cell Separating Apparatus and Cancer Cell Separating Method FIG. 1 is a cross-sectional view diagrammatically showing a cancer cell separating apparatus 10 according to a first embodiment of the invention and FIG. 2 is an enlarged cross-sectional view of the cancer cell separating apparatus 10 shown in FIG. 1 for explaining a cancer cell separating method with the cancer cell separating apparatus 10.

The cancer cell separating apparatus 10 according to the first embodiment has a function to selectively separate cancer cells 20 from non-cancer cells (cells other than cancer cells) 24 in a cell slurry 26. In this specification, the term "cancer cells" means malignant tumor cells. The cell slurry 26 is liquid including at least cells and is liquid which may include cancer cells and, for example, is liquid including the cancer cells and non-cancer cells. As the cell slurry 26, body fluids such as blood, lymph fluid, salivarius, urine, tear fluid are exemplified.

The cancer cell separating apparatus 10 according to the first embodiment includes a flow channel 11. The flow channel 11 includes an antibody fixation area 12 having antibodies 13 which specifically binds to the cancer cells 20 fixed thereto. In the cancer cell separating apparatus 10 according to the first embodiment, as shown in FIG. 1 and FIG. 2, the antibody fixation area 12 is provided entirely on the surface (a surface coming into contact with the cell slurry 26) of the flow channel 11.

As the antibody 13 which is specifically bound to the cancer cell 20, an antibody against a surface antigen 22 of the cancer cell 20 is exemplified. In the cancer cell separating apparatus 10 according to the first embodiment, a case where the antibody 13 against the surface antigen 22 of the cancer cell 20 is used as the antibody 13 which is specifically bound to the cancer cell 20 will be described. In this case, the antibody 13 against the surface antigen 22 of the cancer cell 20 may be selected according to the type of the cancer cell 20 to be separated. For example, as an antibody against a surface antigen common to epithelial cancer, Ep-CAM antibody and N-cadherin antibody are exemplified. As an antibody against a surface antigen specific for mammary cancer, HER2 antibody is exemplified. As an antibody against a surface antigen specific for colon cancer, NS19-9 antibody is exemplified. As an antibody against a surface antigen specific for prostatic cancer, CD49, CD54, and CD 59 antibodies are exemplified. The antibodies exemplified above may be used as the antibody 13.

Fixation of the antibodies 13 in the antibody fixation area 12 may be achieved by a method on the basis of physical adsorption or a method on the basis of chemical binding. The method on the basis of the chemical binding is effective in that reliable fixation is ensured. For example, when the surface is formed of a material including hydroxyl group, the antibodies can be fixed to the surface on the basis of the chemical binding by transforming carboxyl group in the antibodies into active ester group, and then causing the hydroxyl group and the active ester group to react.

The cancer cell separating apparatus 10 according to the first embodiment is configured to separate the cancer cells 20 from the non-cancer cells 24 using a difference in velocity of movement between the cancer cells 20 and the non-cancer cells 24 in the cell slurry 26 introduced into the flow channel 11.

More specifically, as shown in FIG. 2, the surface antigens 22 of the cancer cells 20 bind specifically to the antibodies 13 and move as if they roll over the surface of the flow channel 11. Therefore, the velocity of movement of the surface antigens 22 in the flow channel 11 is slow. In contrast, since the non-cancer cells 24 are not bound to the antibodies 13, they move in the flow channel 11 at a velocity higher than the cancer cells 20. Accordingly, there arises a difference in velocity of movement between the cancer cells 20 and the non-cancer cells 24. Therefore, cells drained from the flow channel 11 within a predetermined period are the non-cancer cells 24, and cells drained from the flow channel 11 after an elapse of the predetermined period from the flow channel 11 of the non-cancer cells 24 are the cancer cells 20. Therefore, separation of the cancer cells 20 from the non-cancer cells 24 is achieved by collecting the cells drained from the flow channel 11 within the predetermine period from an introduction of the cell slurry 26 into the flow channel 11 as the non-cancer cells 24, and collecting the cells drained from the flow channel 11 after the elapse of the predetermined period from the introduction of the cell slurry 26 into the flow channel 11 as the cancer cells 20.

As the cancer cells 20 to be separated, circulating cancer cells (CTC) are exemplified. When the cell slurry 26 is the blood or the lymph fluid, the metastasis of cancer of a patient is reliably restrained by removing the CTC from blood or lymph fluid taken from the patient using the cancer cell separating apparatus 10 according to the first embodiment and returning the blood or the lymph fluid again into the body of the patient. For example, by selectively separating the CTC from the blood, not only the CTC may be separated from other components (for example, normal cells such as red blood cells, white blood cells, blood platelet, and so on, salts, blood plasma protein such as albumin, antibodies such as immunoglobulin, blood coagulation factors), but also damages to the non-cancer cells and components are minimized. The body fluid may be diluted.

Also, removal of the cancer cells (CTC) using the cancer cell separating apparatus 10 according to the first embodiment may be combined with the radiatherapeutics and/or chemotherapeutics, or may be used as a substitution of the radiatherapeutics or the chemotherapeutics. In other words, a method of treating and/or preventing cancers according to the first embodiment of the invention includes removing cancer cells from body fluid taken from a patient using the cancer cell separating apparatus 10 according to the first embodiment and then returning the body fluid into the body of the patient. In this case, returning the body fluid into the body of the patient may be achieved with the same method as hemodialysis.

The cancer cell separating apparatus 10 according to the first embodiment may be used as an apparatus for separating cells other than the cancer cells, virus, bacteria, protein, low-molecule and high-molecule compound, particles, colloid, allergic substances such as pollen, toxic agents, harmful substances, environment contaminating substances from liquid. The cancer cell separating apparatus 10 according to the first embodiment may also be used as an apparatuses, for example, for hemodialysis, hemocatharisis, cell differentiation-induction, or gene introduction, or as an disease germs removing device (water purification filter).

1.2. Effects and Advantages
(i) General Cell Separating Method

In a cell separating method generally used for separating minute and small quantity of cells, separation of target cells is performed using a physical method and a chemical method after having differentiated the target cells and cells other than the target cells by dyeing the target cells, or caused the target cells to be chemically bound to particles.

(ii) Cancer Cell Separating Apparatus 10 According to the First Embodiment

In contrast, according to the cancer cell separating apparatus 10 in the first embodiment, damages to the cells are minimized, and the cancer cells 20 may be removed selectively and with high degree of accuracy by separating the cancer cells 20 from non-cancer cells 24 using the difference in velocity of movement between the cancer cells 20 and the non-cancer cells 24 in the cell slurry 26 introduced into the flow channel 11. Since a flow channel having a complicated structure is not necessary for separating the cancer cells 20, the cancer cells 20 can be separated by the flow channel 11 in a simple structure, so that reduction of cost required for manufacturing the flow channel is achieved. Furthermore, by selecting the types of the antibodies 13 to be fixed to the surface of the flow channel 11, removal of a wide variety of the cancer cells 20 is accommodated.

In the description of a second embodiment to a seventh embodiment described below, the same configurations as the first embodiment are designated with the same reference numerals, and detailed description is omitted.

Figure 3:
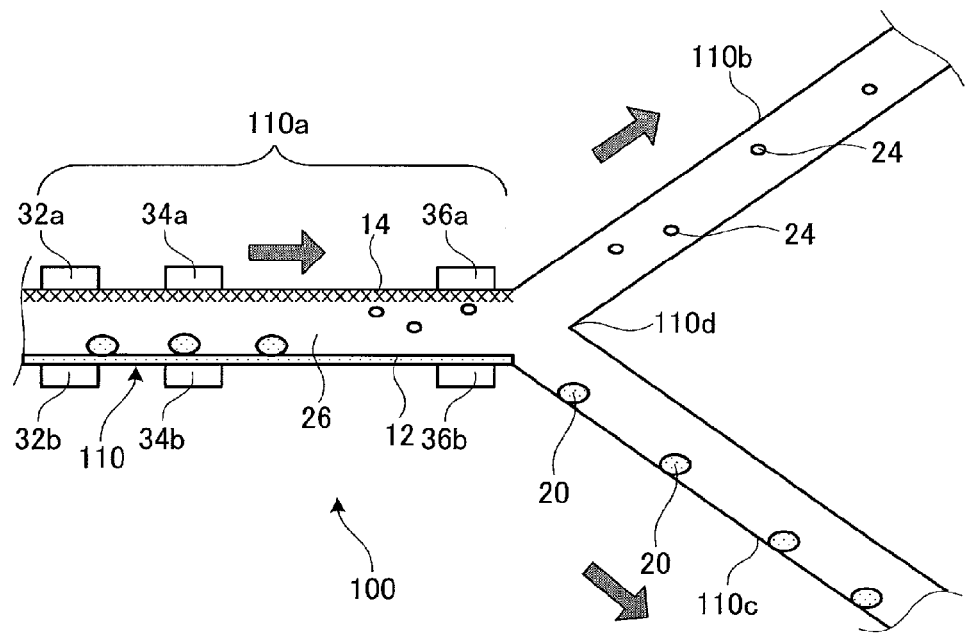
FIG. 3 is a cross-sectional view diagrammatically showing a cancer cell separating apparatus according to a second embodiment of the invention.

2. Second Embodiment 2.1. Configuration of Cancer Cell Separating Apparatus and Method of Usage FIG. 3 is a drawing diagrammatically showing a cross section of a cancer cell separating apparatus 100 according to the second embodiment.

The cancer cell separating apparatus 100 according to the second embodiment is different in configuration from the cancer cell separating apparatus 10 according to the first embodiment in that (i) a flow channel 110 includes a first portion 110a, and a second portion 110b and a third portion 110c bifurcated from an one end portion of the first portion 110a, and in that (ii) a first electrode pair 32a and 32b, a second electrode pair 34a and 34b, and a dielectric migration electrode pair 36a and 36b are provided respectively so as to interpose the flow channel 110.

The cancer cell separating apparatus 100 according to the second embodiment is configured to separate the cancer cells 20 from the non-cancer cells 24 using a difference in velocity of movement between the cancer cells 20 and the non-cancer cells 24 in the cell slurry 26 introduced into the flow channel 110 in the same manner as the cancer cell separating apparatus 10 according to the first embodiment. The difference in velocity of movement may be detected by the physical methods (for example, conductivity, impedance, light sensing).

The cancer cell separating apparatus 100 according to the second embodiment is capable of detecting time lengths required for the cancer cells 20 and the non-cancer cells 24 to pass from the first electrode pair 32a and 32b to the second electrode pair 34a and 34b, respectively. In the cancer cell separating apparatus 100 in the second embodiment, flow velocity of the cell slurry 26 in the flow channel 110 is preferably set to a velocity which allows detection of one single cell passing from the first electrode pair 32a and 32b to the second electrode pair 34a and 34b so that whether the cell passing from the first electrode pair 32a and 32b to the second electrode pair 34a and 34b is the cancer cell 20 or the non-cancer cell 24 can be determined.

As described later, the cancer cell separating apparatus 100 according to the second embodiment is capable of detecting a first time length required for the cancer cells 20 to pass from the first electrode pair 32a and 32b to the second electrode pair 34a and 34b and a second time length required for the non-cancer cells 24 different from the cancer cells 20 to pass from the first electrode pair 32a and 32b to the second electrode pair 34a and 34b and controlling the dielectric migration electrode pair 36a and 36b on the basis of the first time length and the second time length.

More specifically, as shown in FIG. 3, the surface antigens 22 of the cancer cells 20 bind specifically to the antibodies 13 and move as if they roll over the surface of the flow channel 110. Therefore, the velocity of movement of the surface antigens 22 in the flow channel 110 is slow. In contrast, since the non-cancer cells 24 are not bound to the antibodies 13, they move in the flow channel 110 at a velocity higher than the cancer cells 20. Accordingly, there arises a difference in velocity of movement between the cancer cells 20 and the non-cancer cells 24. Therefore, a first time length ($\Delta t_c$) required for the cancer cells 20 to pass from the first electrode pair 32a and 32b to the second electrode pair 34a and 34b is longer than a second time length ($\Delta t_n$) required for the non-cancer cells 24 to pass from the first electrode pair 32a and 32b to the second electrode pair 34a and 34b.

Therefore, the cancer cell separating apparatus 100 according to the second embodiment detects the time lengths required for a single cell to pass from the first electrode pair 32a and 32b to the second electrode pair 34a and 34b, and determines whether the single cell is the cancer cell 20 or the non-cancer cell 24 on the basis of the time length for such the movement. Accordingly, the cancer cells 20 are separated from the non-cancer cells 24. More specifically, when a time length required for a reference cell to pass from the first electrode pair 32a and 32b to the second electrode pair 34a and 34b is expressed by $\Delta t_{ref}$, if the time length required for a certain cell to pass from the first electrode pair 32a and 32b to the second electrode pair 34a and 34b is shorter than $\Delta t_{ref}$, it is determined that the certain cells is the non-cancer cell 24 ($\Delta t_n < \Delta t_{ref}$). In contrast, if the time length required for a certain cell to pass from the first electrode pair 32a and 32b to the second electrode pair 34a and 34b is longer than $\Delta t_{ref}$, it is determined that the certain cell is the cancer cell 20 ($\Delta t_c > \Delta t_{ref}$). The value $\Delta t_{ref}$ may be determined as needed on the basis of a measured value according to conditions such as the type of the cancer cells 20 and the flow velocity of the cell slurry 26 in the flow channel 110.

According to the cancer cell separating apparatus 100 in the second embodiment, since the dielectric migration electrode pair 36a and 36b are provided on the upstream side from a bifurcated point 110d of the flow channel 110 (in the first portion 110a), the respective cells are controlled so as to move to the second portion 110b or the third portion 110c by controlling a voltage to be applied on the basis of the time length required for the respective cells to move from the first electrode pair 32a and 32b to the second electrode pair 34a and 34b.

For example, in a case where the certain cell is the cancer cell 20, the time length required for moving from the first electrode pair 32a and 32b to the second electrode pair 34a and 34b is longer than the non-cancer cell ($>\Delta t_{ref}$). Therefore, in a case where the time length required for a certain cell to move from the first electrode pair 32a and 32b to the second electrode pair 34a and 34b is longer, the certain cell is determined to be the cancer cell 20, and the certain cell (the cancer cell 20) is moved to the third portion 110c by applying a predetermined voltage to the dielectric migration electrode pair 36a and 36b when the certain cell (the cancer cell 20) moves between the dielectric migration electrode pair 36a and 36b.

In contrast, in a case where a certain cell is the non-cancer cell 24, the time required for moving from the first electrode pair 32a and 32b to the second electrode pair 34a and 34b is shorter than the cancer cell 20 ($<\Delta t_{ref}$). Therefore, in a case where the time length required for a certain cell to move from the first electrode pair 32a and 32b to the second electrode pair 34a and 34b is shorter, the certain cell is determined to be the non-cancer cell 24, and the certain cell (the non-cancer cell 24) is moved to the second portion 110b by applying a predetermined voltage to the dielectric migration electrode pair 36a and 36b when the certain cell (the non-cancer cell 24) passes between the dielectric migration electrode pair 36a and 36b.

The first electrode pair 32a and 32b, the second electrode pair 34a and 34b, and the dielectric migration electrode pair 36a and 36b are electrically or optically connected to a data processing unit (not shown), and the time length required for a certain cell to move from the first electrode pair 32a and 32b to the second electrode pair 34a and 34b is calculated by the data processing unit on the basis of information transmitted from the first electrode pair 32a and 32b and the second electrode pair 34a and 34b to the data processing unit, and whether the certain cell is the cancer cell 20 or the non-cancer cell 24 is determined by the data processing unit on the basis of the calculated time length. Subsequently, on the basis of the result of determination, a predetermined voltage is applied to the dielectric migration electrode pair 36a and 36b according to the types of the cancer cells.

In the example shown above, the case where the cancer cells 20 and the non-cancer cells 24 are determined by the first electrode pair 32a and 32b and the second electrode pair 34a and 34b, and the dielectric migration electrode pair 36a and 36b are controlled for individual cells has been exemplified. However, the dielectric migration electrode pair 36a and 36b may be controlled in other methods.

For example, it is also possible to control in such a manner that the dielectric migration electrode pair 36a and 36b are controlled so as to move the cells to the third portion 110c for a certain period of time after having sensed the fact that the cancer cell 20 has passed through with the first electrode pair 32a and 32b and the second electrode pair 34a and 34b. As the certain period of time, for example, a time period required for a standard cancer cell 20 to move from the second electrode pair 34a and 34b to the dielectric migration electrode pair 36a and 36b is exemplified.

According to the cancer cell separating apparatus 100 in the second embodiment, as shown in FIG. 3, an antibody fixation prohibited area 14 where the antibodies 13 are not fixed is provided on a surface of the first portion 110a closer to the second portion 110b, and the antibody fixation area 12 is provided on the surface of the first portion 110a closer to the third portion 110c. Accordingly, in the first portion 110a, the cancer cells 20 move in the vicinity of the antibody fixation area 12 of the flow channel 110 while being bound to the antibodies 13, while the non-cancer cells 24 move in the flow channel 110 without being bound to the antibodies 13. Accordingly, the cancer cells 20 are guided to the third portion 110c and the non-cancer cells 24 are guided to the second portion 110b. Accordingly, the cancer cells 20 and the non-cancer cells 24 are separated further reliably.

3. Third Embodiment 3.3. Configuration of Cancer Cell Separating Apparatus and Method of Usage FIG. 4 is a drawing diagrammatically showing a cross section of a cancer cell separating apparatus 200 according to a third embodiment.

The cancer cell separating apparatus 200 according to the third embodiment is different from the cancer cell separating apparatus 100 according to the second embodiment in that the antibody fixation area 12 is provided also on a third portion 210c of a flow channel 210, but has the same configuration as the cancer cell separating apparatus 100 according to the second embodiment other than the above-described point. Therefore, the cancer cell separating apparatus 200 according to the third embodiment achieves the same effects and advantages as the cancer cell separating apparatus 100 according to the second embodiment. The method of using the cancer cell separating apparatus 200 according to the third embodiment is the same as that of the cancer cell separating apparatus 100 according to the second embodiment.

Figure 4:
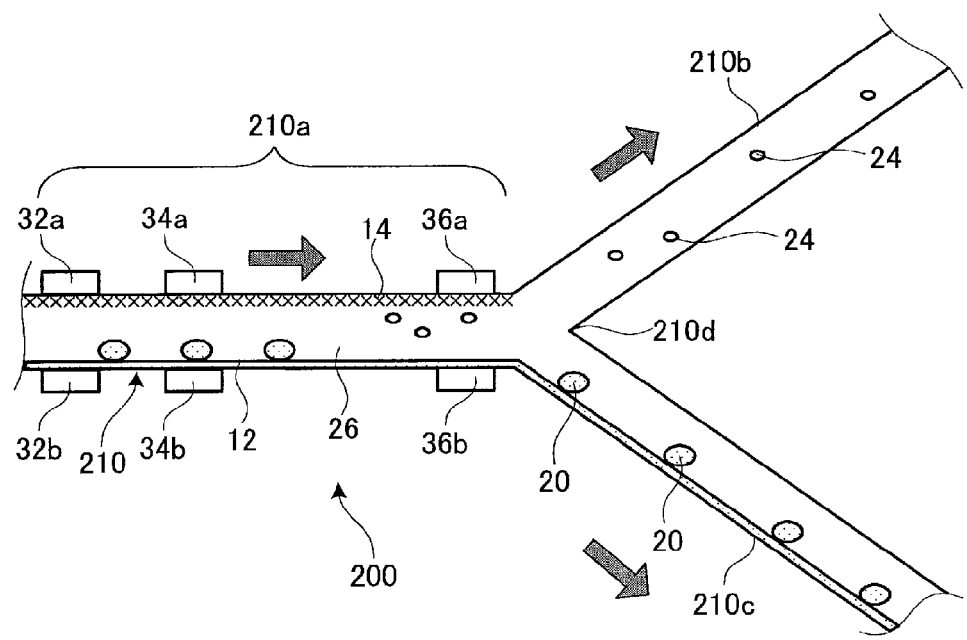
FIG. 4 is a cross-sectional view diagrammatically showing a cancer cell separating apparatus according to a third embodiment of the invention.

In the cancer cell separating apparatus 200 in the third embodiment, as shown in FIG. 4, the antibody fixation prohibited area 14 where the antibodies 13 are not fixed is provided on the surface of a first portion 210a on the side of a second surface 210b, and the antibody fixation area 12 is provided on the surface of the first portion 210a on the side of a third surface 210c in the same manner as the cancer cell separating apparatus 100 in the second embodiment. Accordingly, in the first portion 210a, the cancer cells 20 move in the vicinity of the antibody fixation area 12 while being bound to the antibodies 13, and hence the cancer cells 20 are susceptible to movement to the third portion 210c. Consequently, the cancer cells 20 are guided to the third portion 210c further easily. Accordingly, the cancer cells 20 and the non-cancer cells 24 are reliably separated.

The cancer cell separating apparatus 200 according to the third embodiment is provided with the antibody fixation area 12 also in the third portion 210c of the flow channel 210 as shown in FIG. 4. More specifically, the antibody fixation area 12 is provided on one side of the third portion 210c (the same side in the first portion 210a as the side where the antibody fixation area 12 is provided). Therefore, in the third portion 210c as well, the cancer cells 20 move while being bound to the antibodies in the antibody fixation area 12. Consequently, the cancer cells 20 are further reliably guided to the third portion 210c.

4. Fourth Embodiment

4.1. Configuration of Cancer Cell Separating Apparatus

Figure 5:
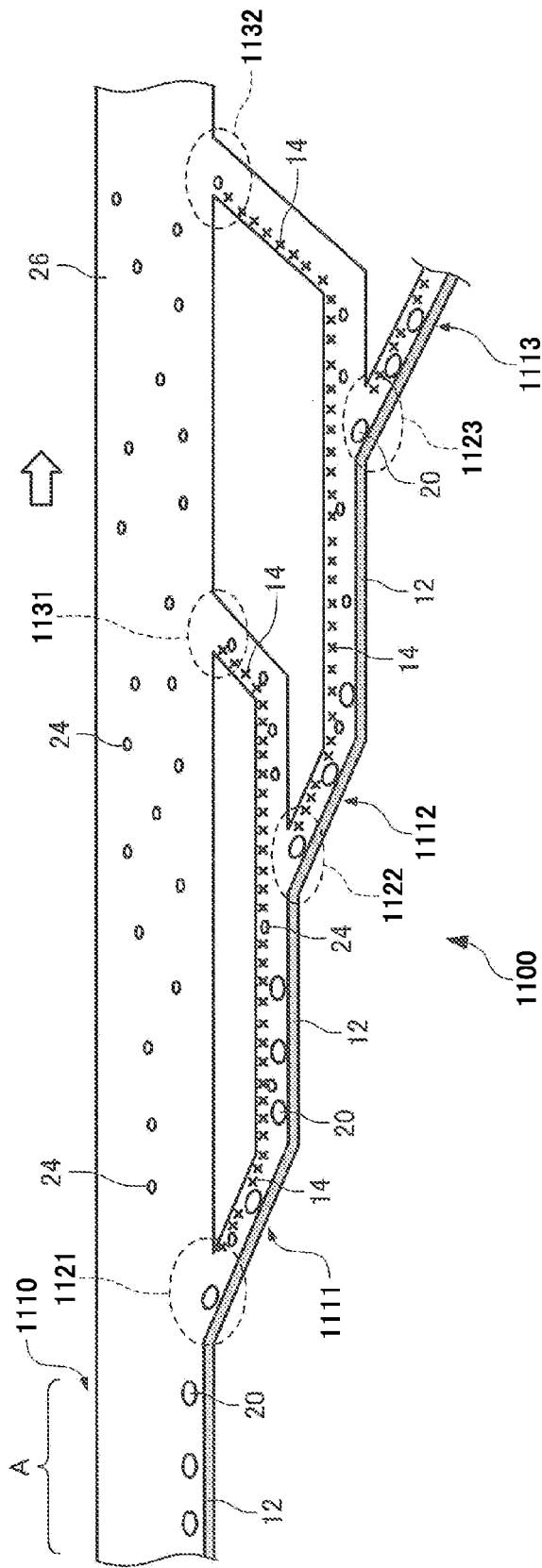
FIG. 5 is a cross-sectional view diagrammatically showing a cancer cell separating apparatus according to a fourth embodiment of the invention.
Figure 6:
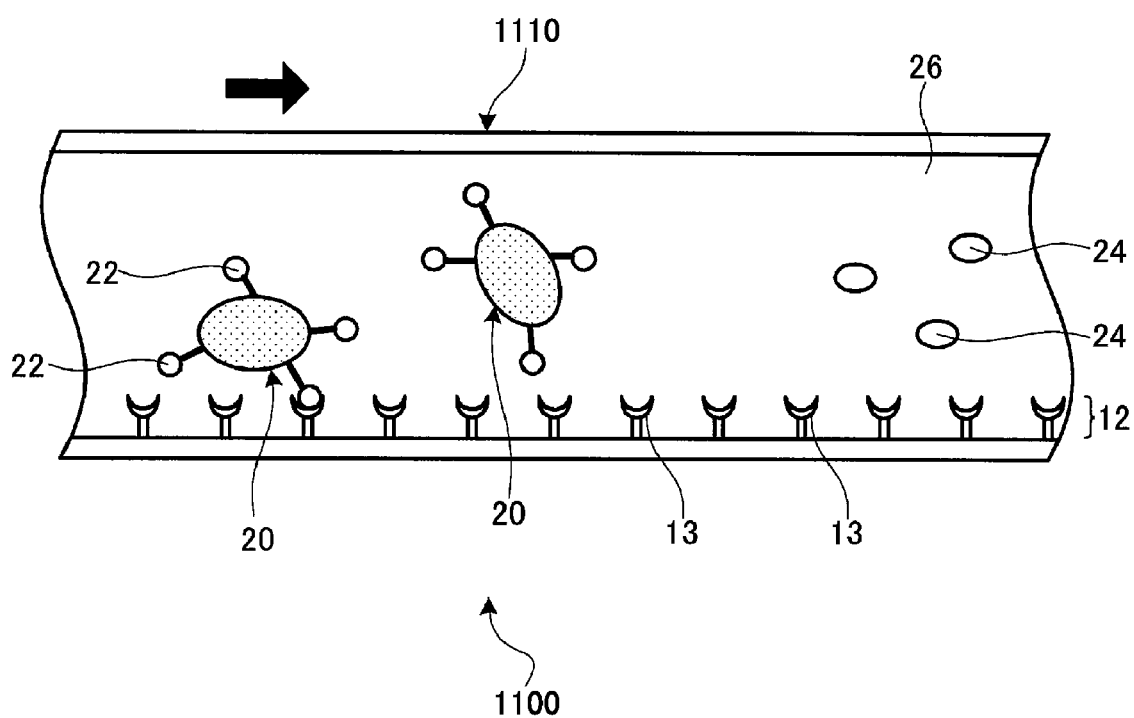
FIG. 6 is an explanatory drawing showing a cancer cell separating method by the cancer cell separating apparatus shown in FIG. 5.

FIG. 5 is a cross-sectional view diagrammatically showing a cancer cell separating apparatus 1100 according to a fourth embodiment of the invention and FIG. 6 is an enlarged cross-sectional view of an area A of the cancer cell separating apparatus 1100 shown in FIG. 5 for explaining a cancer cell separating method with the cancer cell separating apparatus 1100.

As shown in FIG. 5 and FIG. 6, the cancer cell separating apparatus 1100 according to the fourth embodiment has a function to selectively separate the cancer cells 20 from the non-cancer cells (cells other than cancer cells) 24 in the cell slurry 26 in the same manner as the first embodiment.

The cancer cell separating apparatus 1100 according to the fourth embodiment includes a primary flow channel 1110 for allowing induction of the cell slurry 26 and a first secondary flow channel 1111. The cell slurry 26 moves in a flow channel in the cancer cell separating apparatus 1100 according to the fourth embodiment in the direction indicated by an arrow in FIG. 5.

The primary flow channel 1100 includes the antibody fixation area 12 having antibodies 13 which specifically bind to the cancer cells 20 fixed thereto. More specifically, the antibody fixation area 12 is provided on an inner wall surface of the primary flow channel 1110 (the wall surface on the side which comes into contact with the cell slurry 26, hereinafter) on the side of the first secondary flow channel 1111. The cell slurry 26 moving in the primary flow channel 1110 is collected or returned to the body after having been subjected to the removal of the cancer cells 20. In other words, the primary flow channel 1110 is connected to a mechanism for collecting the cell slurry 26 or to a mechanism for returning the same back to the body (not shown).

As shown in FIG. 5, the first secondary flow channel 1111 is branched from a first branch portion 1121 provided in the primary flow channel 1110, and joins the primary flow channel 1110 at a first joint portion 1131 provided at a predetermined distance from the first branch portion 1121 of the primary flow channel 1110 (a position proceeded from the first branch portion 1121 in the direction indicated by an arrow (the direction of movement of the cell slurry 26)).

Also, the inner wall surface of the first secondary flow channel 1111 is provided with the antibody fixation area 12 on the side apart from the primary flow channel 1110. More specifically, in the cancer cell separating apparatus 1100 according to the fourth embodiment, the first secondary flow channel 1111 is provided with the antibody fixation area 12 between the first branch portion 1121 and a second branch portion 1122 of the inner wall surface on the side apart from the primary flow channel 1110. In addition, the cancer cell separating apparatus 1100 according to the fourth embodiment is provided with the antibody fixation prohibited area 14 having no antibody 13 fixed thereon on the inner wall surface of the first secondary flow channel 1111 on the side close to the primary flow channel 1110.

The cancer cell separating apparatus 1100 according to the fourth embodiment may further include a second secondary flow channel 1112. As shown in FIG. 5, the second secondary flow channel 1112 is branched from the second branch portion 1122 provided in the first secondary flow channel 1111, and joins the primary flow channel 1110 at a second joint portion 1132 provided at a predetermined distance from the first joint portion 1131 of the primary flow channel 1110 (a position proceeded from the first joint portion 1131 in the direction of movement of the cell slurry 26)).

Also, the inner wall surface of the second secondary flow channel 1112 is provided with the antibody fixation area 12 on the side apart from the primary flow channel 1110. More specifically, in the cancer cell separating apparatus 1100 according to the fourth embodiment, the second secondary flow channel 1112 is provided with the antibody fixation area 12 between the second branch portion 1122 and a third branch portion 1123 of the inner wall surface on the side apart from the primary flow channel 1110, and is provided with the antibody fixation prohibited area 14 on the side closer to the primary flow channel 1110. The antibody fixation area 12 and the antibody fixation prohibited area 14 may be provided, for example, into a semi-circular shape on the primary flow channel side or the secondary flow channel side from a mid section of the flow channel.

The cancer cell separating apparatus 1100 according to the fourth embodiment is further provided with a third secondary flow channel 1113 branched from the third branch portion 1123 of the second secondary flow channel 1112. The third secondary flow channel 1113 may be connected, for example, to a mechanism (not shown) configured to collect liquid including the separated cancer cells 20. Alternatively, the cancer cell separating apparatus 1100 according to the fourth embodiment may have a structure in which the third secondary flow channel 1113 is connected to the primary flow channel 1110 at the joint portion (not shown) in the same manner as the second secondary flow channel 1112. In this case, the third secondary flow channel 1113 may be branched from the third branch portion 1123 provided in the second secondary flow channel 1112, and joined with the primary flow channel 1110 at the third joint portion (not shown) provided at a position at a predetermined distance from the second joint portion 1132 of the primary flow channel 1110. Also, the inner wall surface of the third secondary flow channel 1113 may be provided with the antibody fixation area 12 on the side apart from the primary flow channel 1110.

In this manner, the cancer cell separating apparatus 1100 according to the fourth embodiment may be provided with two or more of the secondary flow channels. In other words, the cancer cell separating apparatus 1100 according to the fourth embodiment may further include, for example, second to $n^{th}$ secondary flow channels (n represents integer numbers of 2 or larger). Here, the $k^{th}$ secondary flow channel (here, k represents integer numbers from 2 to n) is branched from the $k^{th}$ branch portion provided in the $k-1^{th}$ secondary flow channel, and joins the primary flow channel 1110 at the $k^{th}$ joint portion provided at a predetermined distance from the $k-1^{th}$ joint portion of the primary flow channel 1110, and the antibody fixation area 12 is provided on the inner wall surface of the $k^{th}$ secondary flow channel apart from the primary flow channel 1110 (Prescription 1).

For example, when the cancer cell separating apparatus 1100 according to the fourth embodiment includes the third secondary flow channel 1113, the third secondary flow channel corresponds to the above-described $k^{th}$ secondary flow channel in the case of k=3, and the third ($k^{th}$) secondary flow channel 1113 is branched from the third ($k^{th}$) branch portion 1123 provided in the second ($k-1^{th}$) secondary flow channel 1112, and joins the primary flow channel 1110 at a third ($k^{th}$) joint portion 1133 provided at a predetermined distance from the second ($k-1^{th}$) joint portion 1132 of the primary flow channel 1110, and the antibody fixation area 12 can be provided on the inner wall surface of the third ($k^{th}$) secondary flow channel 1113 on the side apart from the primary flow channel 1110. Although the case of k=3 has been described above, the invention is not limited to the case of k=3, and the above-described Prescription 1 is applicable to the respective secondary flow channels in a case where two or more secondary flow channels are provided in the cancer cell separating apparatus 1100 according to the fourth embodiment.

4.2. Antibody Fixation Area 12

In the antibody fixation area 12, the same antibodies as those exemplified in the first embodiment may be used as the antibodies 13 to be bound specifically to the cancer cells 20, and the fixation of the antibodies 13 is also the same.

4.3. Target to be Separated

As the cancer cells 20 to be separated, for example, the circulating cancer cells (CTC) is exemplified as in the first embodiment.

Also, removal of the cancer cells (CTC) using the cancer cell separating apparatus 1100 according to the fourth embodiment may be combined with the radiatherapeutics and/or chemotherapeutics, or may be used as a substitution of the radiatherapeutics or the chemotherapeutics.

In the same manner as the first embodiment, the cancer cell separating apparatus 1100 according to the fourth embodiment may be used as an apparatus for separating cells other than the cancer cells, virus, bacteria, protein, low-molecule and high-molecule compound, particles, colloid, allergic substances such as pollen, toxic agents, harmful substances, environment contaminating substances from liquid.

4.4. Cancer Cell Separating Method Using Cancer Cell Separating Apparatus

The cancer cell separating apparatus 1100 according to the fourth embodiment is configured to separate the cancer cells 20 from the non-cancer cells 24 using a difference in velocity of movement between the cancer cells 20 and the non-cancer cells 24 in the cell slurry 26 introduced into the primary flow channel 1110. The difference in velocity of movement may be detected by physical methods (for example, conductivity, impedance, light sensing).

More specifically, as shown in FIG. 6, the surface antigens 22 of the cancer cells 20 bind specifically to the antibodies 13 and move as if they roll over the inner wall surface of the flow channel (primary flow channel 1110 in FIG. 6). Therefore, the velocity of movement of the surface antigens 22 in the flow channel is slow. In contrast, since the non-cancer cells 24 are not bound to the antibodies 13, they move in the flow channel at a velocity higher than the cancer cells 20. Accordingly, there arises a difference in velocity of movement between the cancer cells 20 and the non-cancer cells 24.

According to the cancer cell separating apparatus 1100 in the fourth embodiment, the primary flow channel 1110 in which the cell slurry 26 is introduced and the first secondary flow channel 1111 are included, and the antibody fixation areas 12 are provided on the inner wall surface of the primary flow channel 1110 on the side of the first secondary flow channel 1111 and on the inner wall surface of the first secondary flow channel 1111 on the side apart from the primary flow channel 1110. Accordingly, in the first secondary flow channel 1111, when the cancer cells 20 which are not removed in the primary flow channel 1110 exist as an assumption, these cancer cells 20 move in the first secondary flow channel 1111 while being bound to the antibodies 13 in the antibody fixation area 12 provided on the inner wall surface of the first secondary flow channel 1111 on the side apart from the primary flow channel 1110. Therefore, since the cancer cells 20 can be guided from the first secondary flow channel 1111 to the second secondary flow channel 1112 via the second branch portion 1122, the cancer cells 20 and the non-cancer cells 24 are reliably separated. Also, damages to the non-cancer cells 24 are little and the cancer cells 20 are removed selectively at high degree of accuracy. Furthermore, by selecting the types of the antibodies 13 to be fixed to the antibody fixation area 12, removal of a wide variety of the cancer cells 20 is accommodated.

As shown in FIG. 5, the cancer cell separating apparatus 1100 according to the fourth embodiment is provided with the antibody fixation-prohibited area 14 having no antibody 13 fixed thereon on the inner wall surface of the first secondary flow channel 1111 on the side close to the primary flow channel 1110. Accordingly, in the first secondary flow channel 1111, the cancer cells 20 move in the vicinity of the antibody fixation area 12 of the first secondary flow channel 1111 while being bound to the antibodies 13, while the non-cancer cells 24 move in the vicinity of the antibody fixation prohibited area 14 of the first secondary flow channel 1111 without being bound to the antibodies 13 when the non-cancer cells 24 enter the first secondary flow channel 1111. Accordingly, the non-cancer cells 24 may be guided from the first secondary flow channel 1111 to the primary flow channel 1110 via the first joint portion 1131. Accordingly, the cancer cells 20 and the non-cancer cells 24 are separated further reliably.

In addition, according to the cancer cell separating apparatus 1100 in the fourth embodiment, the first secondary flow channel 1111 is branched from the first branch portion 1121 provided in the primary flow channel 1110, and joins the primary flow channel 1110 at the first joint portion 1131, so that the non-cancer cells 24 and components in the cell slurry 26 after having separated the cancer cells 20 may be guided to the primary flow channel 1110. Accordingly, the non-cancer cells 24 and components in the cell slurry 26 can be collected, and hence loss of components in the cell slurry 26 other than the cancer cells 20 is prevented. Therefore, when the cell slurry 26 after having removed the cancer cell 20 by the cancer cell separating apparatus 1100 according to the fourth embodiment is used by returning to the body of a human or an animal other than the human, since the loss of the components other than the cancer cells 20 in the cell slurry 26 is restrained, it functions effectively in the body.

In addition, according to the cancer cell separating apparatus 1100 in the fourth embodiment, the antibody fixation area 12 is provided on the inner wall surface of the second secondary flow channel 1112 on the side apart from the primary flow channel 1110. Accordingly, in the first secondary flow channel 1111, when the cancer cells 20 which are not removed exist as an assumption, these cancer cells 20 move in the second secondary flow channel 1112 while being bound to the antibodies 13 in the antibody fixation area 12 provided on the inner wall surface of the second secondary flow channel 1112 on the side apart from the primary flow channel 1110. Accordingly, the cancer cells 20 may be guided from the second secondary flow channel 1112 to the third secondary flow channel 1113 via the third branch portion 1123. Accordingly, the cancer cells 20 and the non-cancer cells 24 are separated further reliably.

In addition, as shown in FIG. 5, the cancer cell separating apparatus 1100 according to the fourth embodiment is provided with the antibody fixation prohibited area 14 having no antibody 13 fixed thereon on the inner wall surface of the second secondary flow channel 1112 on the side close to the primary flow channel 1110. Accordingly, in the second secondary flow channel 1112, the cancer cells 20 move in the vicinity of the antibody fixation area 12 of the second secondary flow channel 1112 while being bound to the antibodies 13, while the non-cancer cells 24 move in the vicinity of the antibody fixation prohibited area 14 of the second secondary flow channel 1112 without being bound to the antibodies 13 when the non-cancer cells 24 enter the second secondary flow channel 1112. Accordingly, the non-cancer cells 24 may be guided from the second secondary flow channel 1112 to the primary flow channel 1110 via the second joint portion 1132. Accordingly, the cancer cells 20 and the non-cancer cells 24 are separated further reliably.

In the cancer cell separating apparatus 1100 according to the fourth embodiment shown in FIG. 5, a case where the first to third secondary flow channels 1111 to 1113 are provided is exemplified. However, the secondary flow channels may be provided four or more and, in this case, the respective secondary flow channels may have the same structure as the second secondary flow channel 1112. Since the quantity of removal of the cancer cells 20 is proportional to the number of the secondary flow channels provided in the cancer cell separating apparatus 1100 according to the fourth embodiment, further effective separation of the cancer cells is achieved.

5. Fifth Embodiment

5.1. Configuration of Cancer Cell Separating Apparatus and Method of Usage

Figure 7:
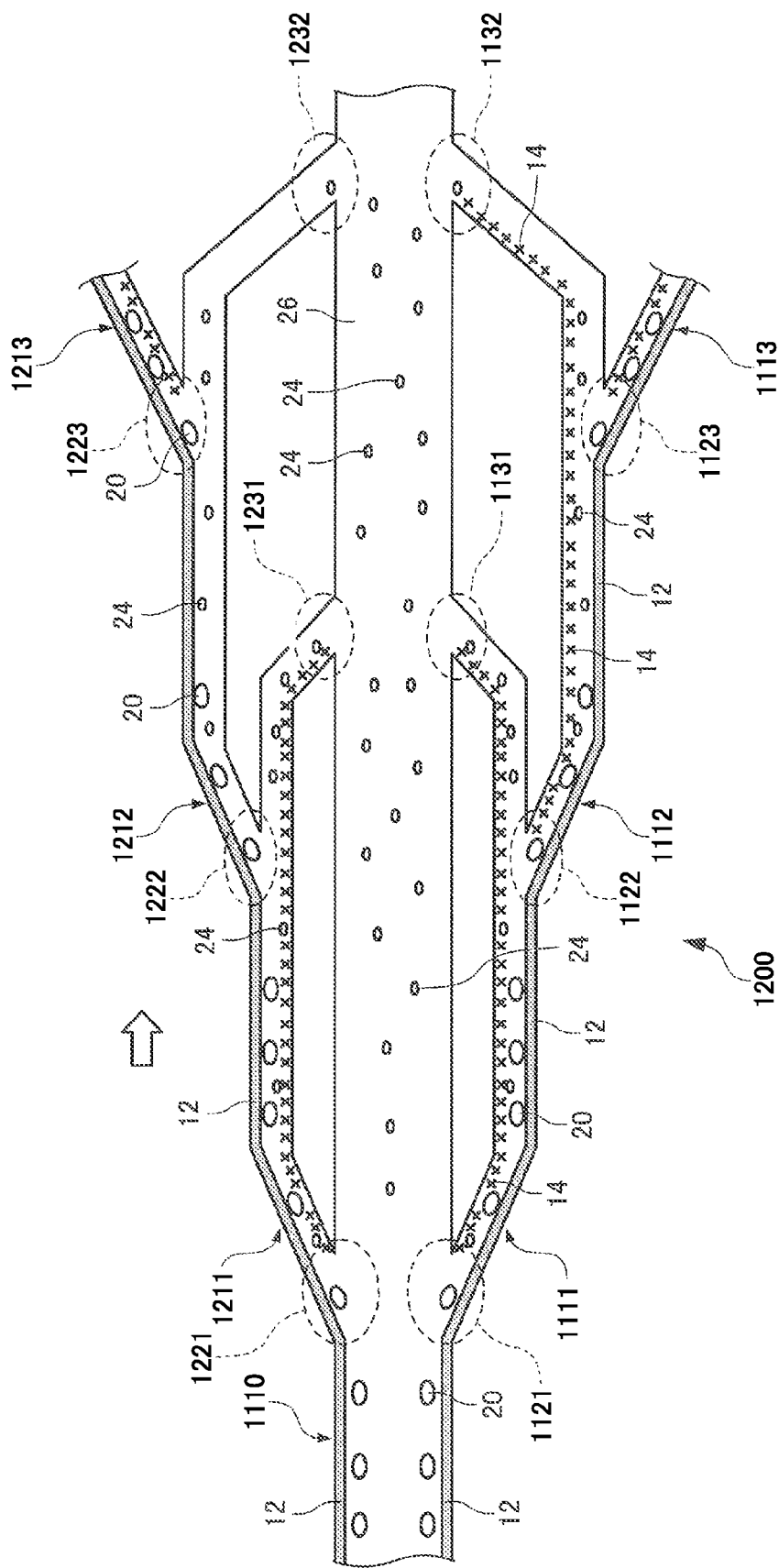
FIG. 7 is a cross-sectional view diagrammatically showing a cancer cell separating apparatus according to a fifth embodiment of the invention.

FIG. 7 is a drawing diagrammatically showing a cross section of a cancer cell separating apparatus 1200 according to a fifth embodiment.

The cancer cell separating apparatus 1200 has a configuration different from the cancer cell separating apparatus 1100 according to the fourth embodiment in that first to third secondary flow channels 1211 to 1213 are further provided in the primary flow channel 1110. In other words, as shown in FIG. 7, the cancer cell separating apparatus 1200 according to the fifth embodiment is provided with the first to third secondary flow channels 1111 to 1113 and the first to third secondary flow channels 1211 to 1213 so as to interpose the primary flow channel 1110 therebetween.

The cancer cell separating apparatus 1200 according to the fifth embodiment is configured to separate the cancer cells 20 from the non-cancer cells 24 using a difference in velocity of movement between the cancer cells 20 and the non-cancer cells 24 in the cell slurry 26 introduced into the primary flow channel 1110 in the same manner as the cancer cell separating apparatus 1100 according to the fourth embodiment.

As shown in FIG. 7, the first to third secondary flow channels 1211 to 1213, first to third branch portions 1221 to 1223, and first and second joint portions 1231 and 1232 have substantially the same structure as the first to third secondary flow channels 1111 to 1113, the first to third branch portions 1121 to 1123, and the first and second joint portions 1131 and 1132 of the cancer cell separating apparatus 1100 according to the fourth embodiment described above, respectively.

Therefore, the cancer cell separating apparatus 1200 according to the fifth embodiment achieves the same effects and advantages as the cancer cell separating apparatus 1100 according to the fourth embodiment. Since the quantity of removal of the cancer cells 20 is increased with increase in number of the secondary flow channels provided in the cancer cell separating apparatus 1200 according to the fifth embodiment, further effective separation of the cancer cells is achieved in comparison with the cancer cell separating apparatus 1100 according to the fourth embodiment.

6. Sixth Embodiment

6.1. Configuration of Cancer Cell Separating Apparatus and Method of Usage

Figure 8:
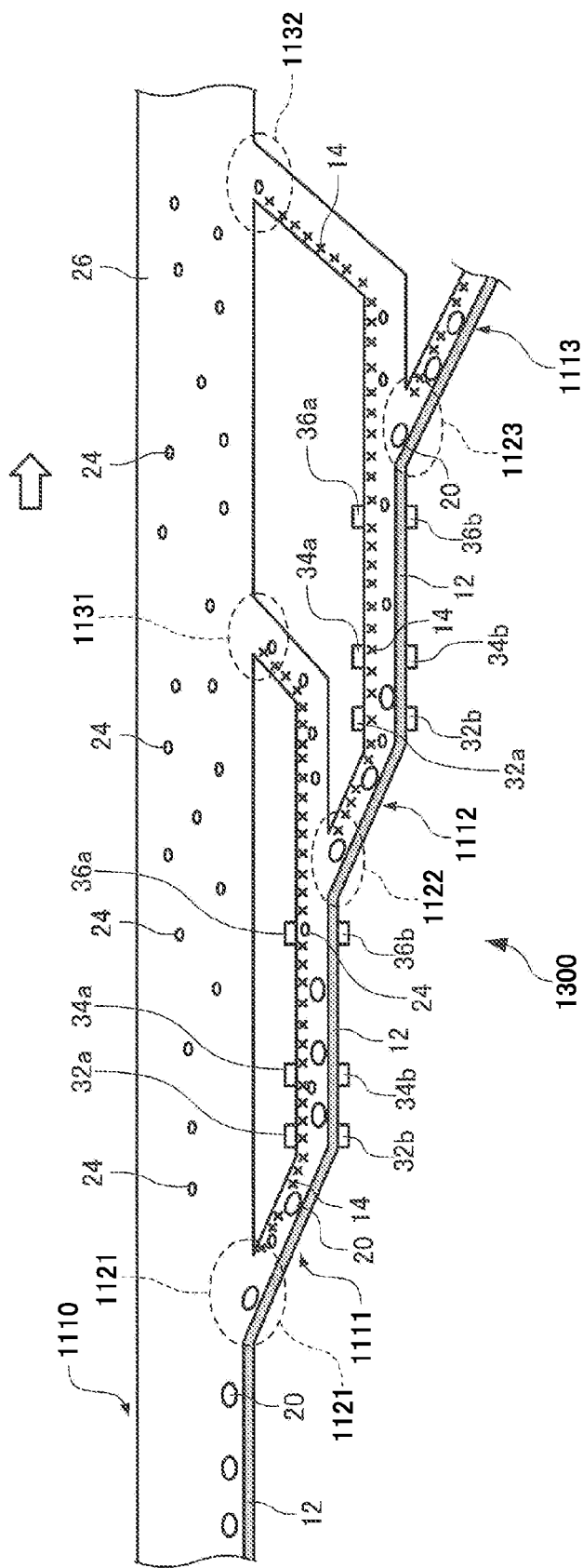
FIG. 8 is a cross-sectional view diagrammatically showing a cancer cell separating apparatus according to a sixth embodiment of the invention.

FIG. 8 is a drawing diagrammatically showing a cross section of a cancer cell separating apparatus 1300 according to a sixth embodiment.

The cancer cell separating apparatus 1300 according to the sixth embodiment has a configuration different from the cancer cell separating apparatus 1100 according to the fourth embodiment in that the first electrode pair 32a and 32b, the second electrode pair 34a and 34b, and the dielectric migration electrode pair 36a and 36b are provided so as to interpose the first and second secondary flow channels 1111 and 1112 respectively. More specifically, the cancer cell separating apparatus 1300 according to the sixth embodiment is provided with the second electrode pair 34a and 34b downstream of the first electrode pair 32a and 32b and the dielectric migration electrode pair 36a and 36b are provided downstream of the second electrode pair 34a and 34b. Here, the term "downstream" means a position at a smaller distance to the joint portion in the first secondary flow channel. More specifically, for example, the expression, "the second electrode pair 34a and 34b are provided downstream of the first electrode pair 32a and 32b in the first secondary flow channel 1111" means that in the first secondary flow channel 1111, the second electrode pair 34a and 34b are provided at positions closer to the first joint portion 1131 than the first electrode pair 32a and 32b, and the expression "the dielectric migration electrode pair 36a and 36b are provided downstream of the second electrode pair 34a and 34b in the first secondary flow channel 1111" means that in the first secondary flow channel 1111, the dielectric migration electrode pair 36a and 36b are provided at positions closer to the first joint portion 1131 than the second electrode pair 34a and 34b. The configurations of the electrodes described above are the same as those shown in the second embodiment.

The cancer cell separating apparatus 1300 according to the sixth embodiment is configured to separate the cancer cells 20 from the non-cancer cells 24 using a difference in velocity of movement between the cancer cells 20 and the non-cancer cells 24 in the cell slurry 26 introduced into the primary flow channel 1110 in the same manner as the cancer cell separating apparatus 1100 according to the fourth embodiment.

The cancer cell separating apparatus 1300 according to the sixth embodiment is capable of detecting time lengths required for the cancer cells 20 and the non-cancer cells 24 to pass from the first electrode pair 32a and 32b to the second electrode pair 34a and 34b, respectively, in the same manner as the second embodiment. In the cancer cell separating apparatus 1300 in the sixth embodiment, the flow velocity of the cell slurry 26 in the first and second secondary flow channels 1111 and 1112 is preferably set to a velocity which allows detection of one single cell passing from the first electrode pair 32a and 32b to the second electrode pair 34a and 34b so that whether the cell passing from the first electrode pair 32a and 32b to the second electrode pair 34a and 34b is the cancer cell 20 or the non-cancer cell 24 can be determined.

Therefore, the cancer cell separating apparatus 1300 according to the sixth embodiment is capable of detecting the first time length required for the cancer cells 20 to pass from the first electrode pair 32a and 32b to the second electrode pair 34a and 34b and the second time length required for the non-cancer cells 24 different from the cancer cells 20 to pass from the first electrode pair 32a and 32b to the second electrode pair 34a and 34b and controlling the dielectric migration electrode pair 36a and 36b on the basis of the first time length and the second time length in the same manner as the second embodiment.

According to the cancer cell separating apparatus 1300 in the sixth embodiment, since the dielectric migration electrode pair 36a and 36b are provided between the second electrode pair 34a and 34b and the second branch portion 1122 (the third branch portion 1123) of the first secondary flow channel 1111 (the second secondary flow channel 1112), whether the respective cells are to be moved to the second secondary flow channel 1112 (the third secondary flow channel 1113) or to be moved as is in the first secondary flow channel 1111 (the second secondary flow channel 1112) can be controlled by controlling the voltage to be applied on the basis of the time length required for the respective cells to move from the first electrode pair 32a and 32b to the second electrode pair 34a and 34b.

For example, in a case where the certain cell is the cancer cell 20, the time length required for moving from the first electrode pair 32a and 32b to the second electrode pair 34a and 34b is longer than the non-cancer cell ($\geq \Delta t_{ref}$). Therefore, in a case where the time length required for a certain cell to move from the first electrode pair 32a and 32b to the second electrode pair 34a and 34b is $\Delta t_{ref}$ or longer, the certain cell is determined to be the cancer cell 20, and the certain cell (the cancer cell 20) is moved to the second secondary flow channel 1112 (the third secondary flow channel 1113) by applying a predetermined voltage to the dielectric migration electrode pair 36a and 36b when the certain cell (the cancer cell 20) passes between the dielectric migration electrode pair 36a and 36b.

In contrast, in a case where a certain cell is the non-cancer cell 24, the time required for moving from the first electrode pair 32a and 32b to the second electrode pair 34a and 34b is shorter than the cancer cell 20 ($<\Delta t_{ref}$). Therefore, in a case where the time length required for a certain cell to move from the first electrode pair 32a and 32b to the second electrode pair 34a and 34b is shorter than $\Delta t_{ref}$, the certain cell is determined to be the non-cancer cell 24, and the certain cell (the non-cancer cell 24) is moved as is in the first secondary flow channel 1111 (the second secondary flow channel 1112) by applying a predetermined voltage to the dielectric migration electrode pair 36a and 36b when the certain cell (the non-cancer cell 24) passes between the dielectric migration electrode pair 36a and 36b.

In the same manner as the second embodiment, the first electrode pair 32a and 32b, the second electrode pair 34a and 34b, and the dielectric migration electrode pair 36a and 36b are electrically or optically connected to the data processing unit (not shown), and the time length required for a certain cell to move from the first electrode pair 32a and 32b to the second electrode pair 34a and 34b is calculated by the data processing unit on the basis of information transmitted from the first electrode pair 32a and 32b and the second electrode pair 34a and 34b to the data processing unit, and whether the certain cell is the cancer cell 20 or the non-cancer cell 24 is determined by the data processing unit on the basis of the calculated time length. Subsequently, on the basis of the result of determination, a predetermined voltage is applied to the dielectric migration electrode pair 36a and 36b according to the types of the cancer cells.

In the example shown above, the case where the cancer cells 20 and the non-cancer cells 24 are determined by the first electrode pair 32a and 32b and the second electrode pair 34a and 34b, and the dielectric migration electrode pair 36a and 36b are controlled for individual cells has been exemplified. However, the dielectric migration electrode pair 36a and 36b may be controlled in other methods.

For example, it is also possible to control in such a manner that the dielectric migration electrode pair 36a and 36b are controlled so as to move the cells to the second secondary flow channel 1112 (the third secondary flow channel 1113) for a certain period of time after having sensed the fact that the cancer cell 20 has passed through with the first electrode pair 32a and 32b and the second electrode pair 34a and 34b. As the certain period of time, for example, a time period required for a standard cancer cell 20 to move from the second electrode pair 34a and 34b to the dielectric migration electrode pair 36a and 36b is exemplified.

Figure 9:
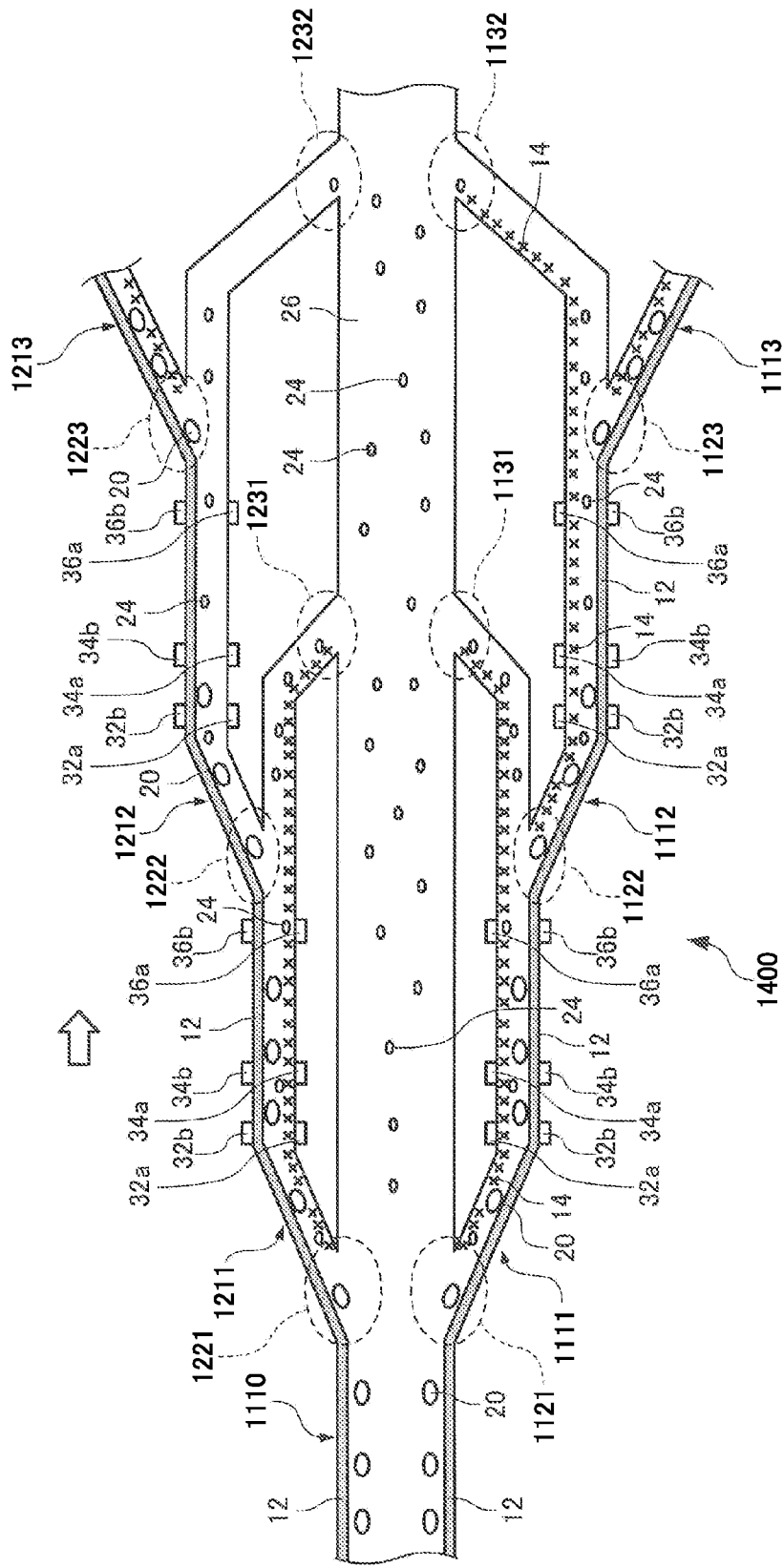
FIG. 9 is a cross-sectional view diagrammatically showing a cancer cell separating apparatus according to a seventh embodiment of the invention.

7. Seventh Embodiment 7.1. Configuration of Cancer Cell Separating Apparatus and Method of Usage FIG. 9 is a drawing diagrammatically showing a cross section of a cancer cell separating apparatus 1400 according to a seventh embodiment.

The cancer cell separating apparatus 1400 according to a seventh embodiment has the same configuration as the cancer cell separating apparatus 1200 according to the fifth embodiment in that the first to third flow channels 1211 to 1213 are provided, and has the same configuration as the cancer cell separating apparatus 1300 according to the sixth embodiment in that the first electrode pair 32a and 32b, the second electrode pair 34a and 34b, and the dielectric migration electrode pair 36a and 36b are provided respectively in the first and second secondary flow channels 1211 and 1212 in the same manner as the first and second secondary flow channels 1111 and 1112. Therefore, the cancer cell separating apparatus 1400 according to the seventh embodiment achieves the same effects and advantages as the cancer cell separating apparatuses 1200 and 1300 according to the fifth and sixth embodiments. The method of using the cancer cell separating apparatus 1400 according to the seventh embodiment is the same as that of the cancer cell separating apparatuses 1200 and 1300 according to the fifth and sixth embodiment.

All of the embodiments of the invention have been described thus far. The invention includes the substantially same configuration as the configuration described in the embodiments (for example, the configuration in which the function, the method, and the result are the same, or the configuration having the same object and the effect). The invention includes also the configuration in which portions which are not essential in the configuration described in the embodiments are replaced. The invention also includes configurations which achieve the same effects and advantages as the configurations described in the embodiments, and configurations which are able to achieve the same object. The invention includes also the configuration including known techniques added to the configuration described in the embodiments.

What is claimed is:

1. A cancer cell separating apparatus comprising:
a primary flow channel for allowing a cell slurry including cancer cells to be introduced therein, the primary flow channel having first and second inner wall surfaces opposite to each other;
a first secondary flow channel having first and second ends that are spaced apart from each other by a predetermined distance, the first end is connected to the primary flow channel at a first branch portion so as to branch from the primary flow channel for directing the cell slurry into the first secondary flow channel, the second end is connected to the primary flow channel at a first joint portion so as to join the first secondary flow channel back to the primary flow channel so that the cell slurry is directed back into the primary flow channel, the first secondary flow channel having third and fourth inner wall surfaces opposite to each other;
an $n^{th}$ secondary flow channel having $2n-1)^{th}$ and $2n^{th}$ ends that are spaced apart from each other, the $(2n-1)^{th}$ end is connected to an $(n-1)^{th}$ secondary flow channel at an $n^{th}$ branch portion so as to branch from the $(n-1)^{th}$ secondary flow channel for directing the cell slurry into the $n^{th}$ secondary flow channel, the $2n^{th}$ end is connected to the primary flow channel at an $n^{th}$ joint portion so as to join the $n^{th}$ secondary flow channel back to the primary flow channel so that the cell slurry is directed back into the primary flow channel, the $n^{th}$ secondary flow channel having $(2n+1)^{th}$ and $(2n+2)^{th}$ inner wall surfaces opposite to each other, where n represents integer numbers of 2 or more; and
an antibody fixation area having antibodies which bind specifically to the cancer cells fixed therein, the antibody fixation area being provided in the primary flow channel, the first secondary flow channel and the $n^{th}$ secondary flow channel, wherein the second and third inner wall surfaces are provided between the first and fourth inner wall surfaces, and the second and $(2n+1)^{th}$ inner wall surfaces are provided between the first and $(2n+2)^{th}$ inner wall surfaces, and the antibody fixation area is provided on the second and fourth inner wall surfaces and the $(2n+2)^{th}$ inner al surfaces.

2. The cancer cell separating apparatus according to claim 1, further comprising:

a first pair of electrodes;

a second pair of electrodes provided downstream from the first pair of electrodes; and a pair of dielectric migration electrodes provided downstream from the second pair of electrodes, wherein the first and second pairs of electrodes detect a first time length for which one of the cancer cells takes to pass from the first pair of electrodes to the second pair of electrodes, the first and second pairs of electrodes detect a second time length for which one non-cancer cell different from the cancer cells takes to pass from the first pair of electrodes to the second pair of electrodes, and the pair of dielectric migration electrodes is controlled on the basis of the first time length and the second time length.

* * * * *